United States Patent [19]

Polly

[11] Patent Number: 4,927,503

[45] Date of Patent: May 22, 1990

[54] METHOD FOR ASSESSMENT OF CORROSION ACTIVITY IN REINFORCED CONCRETE

[75] Inventor: Daniel R. Polly, Oxnard, Calif.

[73] Assignee: The United States of America as represented by the Secretary of the Navy, Washington, D.C.

[21] Appl. No.: 308,596

[22] Filed: Feb. 10, 1989

Related U.S. Application Data

[62] Division of Ser. No. 196,186, May 16, 1988, abandoned.

[51] Int. Cl.⁵ ............................................. G01N 17/02
[52] U.S. Cl. ............................ 204/153.11; 204/404; 204/412; 204/435
[58] Field of Search ............... 204/1 C, 1 T, 400, 404, 204/412, 435, 434

[56] References Cited

U.S. PATENT DOCUMENTS

| | | | |
|---|---|---|---|
| 3,449,232 | 6/1969 | Bailey | 204/435 |
| 3,696,017 | 10/1972 | Wallen | 204/434 |
| 4,155,814 | 5/1979 | Tejaflussy et al. | 204/404 |
| 4,454,006 | 6/1984 | Hausler et al. | 204/404 |
| 4,611,175 | 9/1986 | Kumar et al. | 324/425 |
| 4,623,434 | 11/1986 | Nicholson et al. | 204/404 |
| 4,703,255 | 10/1987 | Strommen | 204/1 C |
| 4,758,324 | 7/1988 | Winneti et al. | 204/147 |
| 4,806,850 | 2/1989 | Saumade et al. | 204/404 |

OTHER PUBLICATIONS

McKensie, "Techniques for Monitoring Corrosion of Steel in Concrete", *Corrosion Prevention & Control*, Feb. 1987, pp. 11-17.

Androde et al, "Quantitative Measurements of Corrosion Rate of Reinforcing Steels Embedded in Concrete Using Polarization Resistance Measurements", *Werkstoffe und Konrian, vol. 29 (1978), pp. 515-519*.

Primary Examiner—T. Tung
Attorney, Agent, or Firm—David S. Kalmbaugh; J. M. St. Amand

[57] ABSTRACT

The probe is a nondestructive testing device for locating and measuring corrosion activity in reinforced concrete structures by direct detection of electrochemical current flow. The device consists of a surface probe valved to present alternative measurement paths when measuring the probe potential with respect to a remote reference electrode, allowing the measurement of IR drops associated with corrosion of reinforcement "rebar". By grid surveys of concrete structures, areas suffering internal corrosion (the primary cause of marine concrete deterioration) can be located and the level of corrosion activity determined.

1 Claim, 2 Drawing Sheets $R_{tube} \ll R_{probe}$

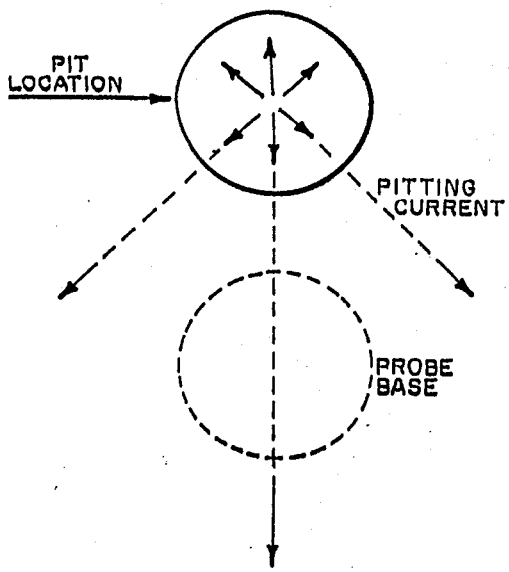
Fig. 4.
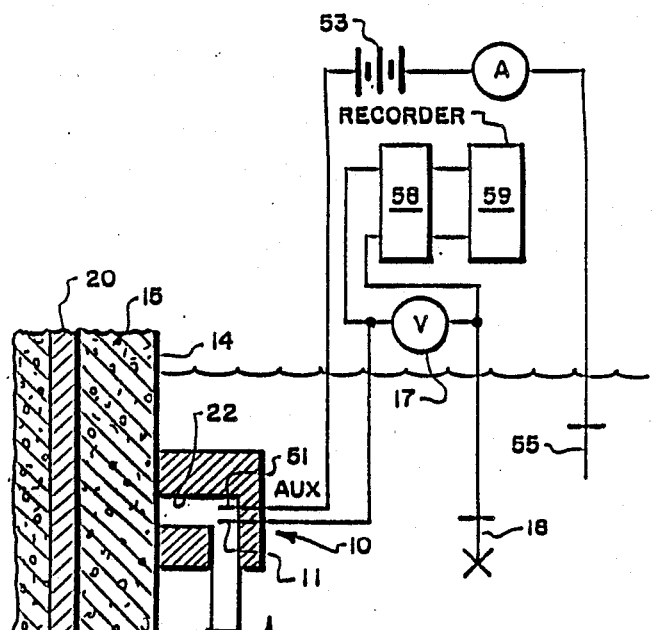
Fig. 5.
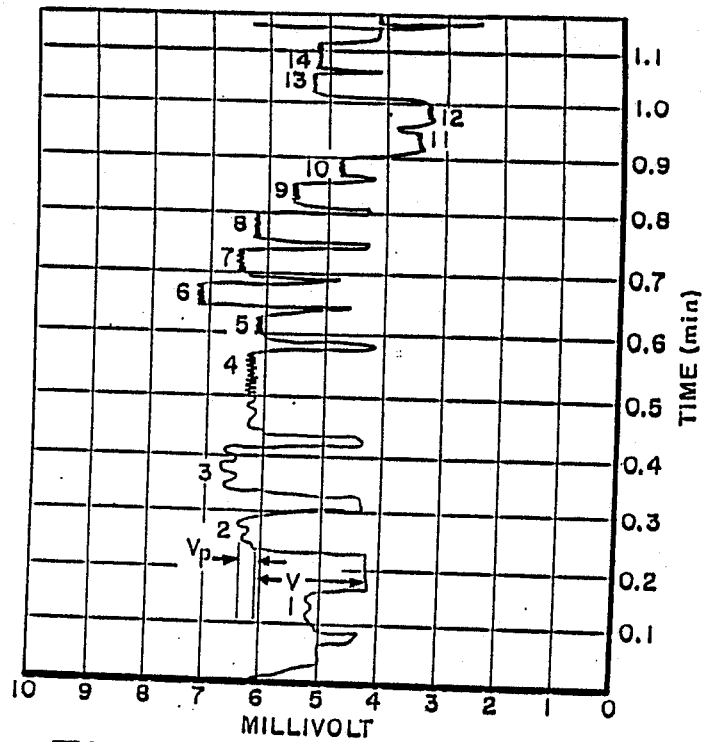
Fig. 6. PROBE RESPONSE RECORDING

METHOD FOR ASSESSMENT OF CORROSION ACTIVITY IN REINFORCED CONCRETE

This is a division of co-pending application Ser. No. 196,186 filed May 16, 1988, abandoned.

FIELD OF THE INVENTION

This invention relates to a method for determining the location and level of reinforcement corrosion activity in concrete structures, and more specifically to a non-destructive testing device for locating and measuring corrosion activity in reinforced concrete structures by direct detection of electrochemical current flow.

BACKGROUND OF THE INVENTION

Corrosion of the metal reinforcement in concrete structures presents a serious threat to durability. It is not the deterioration of the concrete itself, but the corrosion of reinforcement that represents the greatest threat to the durability of concrete structures. Cracking and spalling of concrete under pressures created by the formation of voluminous corrosion products is a common occurence. By determining the extent of corrosion activity, life estimates can be made or preventative measures taken.

Presently, potential measurement methods require electrical connection to the reinforcement, and this only indicates that corrosion has taken place, it does not indicate the level of corrosion activity. The standard method of field investigating of corrosion behavior employs "half-cells" for determining the potential of the reinforcement at selected locations. The basic test configuration is shown in FIG. 1, where a high impedance voltmeter is employed to determine potentials relative to a copper-copper sulfate (Cu/CuSO$_4$) reference electrode. Potential readings at the area of measurement are considered to indicate the following activity:

| | |
|---|---|
| $E_{corr} > -.20$ volts | 90% probality no corrosion |
| $-.20 > E_{corr} > -.35$ volts | Corrosion uncertain |
| $E_{corr} < -.35$ volt | 90% possibility corrosion occurring |

This method of potential measurement can result in useful data for structures such as bridge decks, particularly with the construction of equipotential contour maps. However, it has undeniable limitations. First, electrical connection with the reinforcement is required. Connection in an existing structure requires removal of concrete at numerous sites to insure electrical continuity to all areas being surveyed. This may be impractical for most inspections. Additionally, in highly conductive marine environments, concrete affects readings in a manner similar to nonconductive coatings; greatly increasing in the area associated with a single measurement (decreasing measurement localization). There is also the questionable range of potential between $-0.20$ and $-0.35$ volts (Cu/CuSO$_4$) associated with the standard test method.

Investigation of pitting behavior with instrumented steel samples embedded in concrete clearly showed a drop in potential associated with the onset of pitting. During an induction period where no current flow is observed, a slow decrease in potential occurs. At approximately $-0.25$ volt (saturated calomel electrode [SCE]) there is a marked rise in current accompanied by a sharp drop in potential. This potential, $-0.32$ volt (Cu/CuSO$_4$), is close to the $-0.20$ volt (Cu/SO$_4$) specified as indicative of no corrosion activity. However, below $-0.50$ volt SCE ($-0.57$ volt Cu/CuSO$_4$) current tapers off with a continued decrease in potential. Therefore, potential measurements in themselves may serve more as an indicator of corrosion history (that corrosion has been initiated) than giving the level of corrosion activity.

SUMMARY OF THE INVENTION

Corroding steel reinforcement in a concrete structure pits with the sites of the corrosion being anodic and the remaining surface of the steel reinforcement being cathodic. Electrochemical current flows through the concrete structure between anodic and cathodic sites with the level of current flow at a particular location indicating the rate of corrosion. The present invention is a non-destructive testing device for locating and measuring corrosion activity in reinforced concrete structures by direct detection of this electrochemical current flow. The device consists of a surface probe valved to present alternating measurement paths for current flow when measuring the potential of an internal electrode relative to a remote reference. This allows measurement of IR drops associated with the electrochemical current flow due to corrosion of the reinforcement. By grid surveys of concrete structures, areas suffering internal corrosion, the primary cause of marine concrete deterioration, can be located and the level of activity can be determined.

It is an object of the present invention, therefore, to provide a non-destructive means for locating and measuring corrosion activity in reinforced concrete structures.

Other objects, advantages and novel features of the invention will become apparent from the following detailed description of the invention when considered in conjunction with the accompaning drawings where like reference numerals refer to like components in each of the figures.

BRIEF DESCRIPTION OF THE DRAWINGS

FIG. 4 is a diagram illustrating corrosion pit location and pitting current direction.

FIG. 5 is a schematic diagram showing use and location of an auxiliary electrode in a system as in FIG. 3.

FIG. 6 shows a typical recorder output for probe measurements using a device of the present invention.

DESCRIPTION OF THE PREFERRED EMBODIMENT

Figure 1:
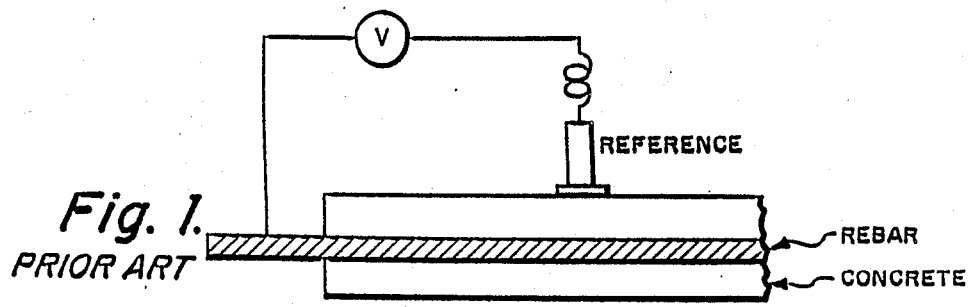
FIG. 1 is a schematic diagram showing a prior art test configuration for measuring to determine if there is any corrosion.
Figure 2:
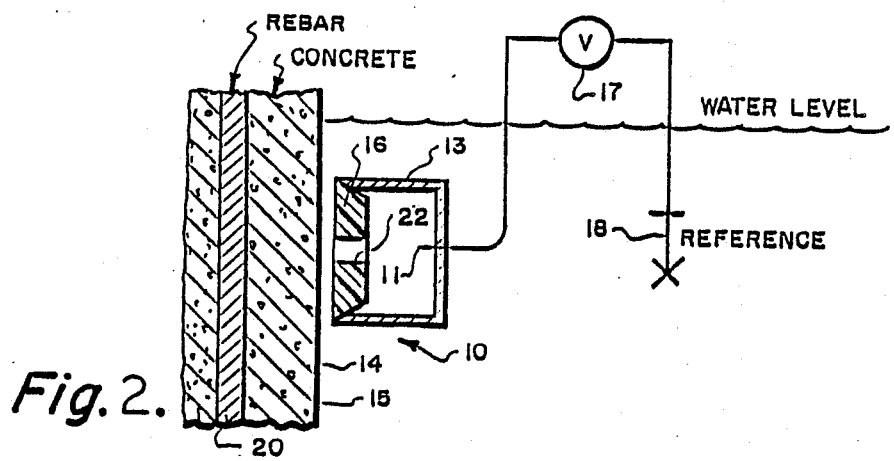
FIG. 2 is a schematic diagram of the preferred embodiment of the invention showing the basic probe system.

Referring to FIG. 2, the basic probe 10 comprises a wire electrode 11 inside a nonconductive shell or housing 13 and a nonconductive base 16. When base 16 is sealed to the surface 14 of a concrete structure 15 a high resistance interface is present between base 16 and surface 14. When sealed against surface 14 the voltage measurement path is through a hole 22 within base 16, the interface between hole 22 and surface 14, and through concrete structure 15. The voltage measured at 17 between the wire electrode 11 and a remote reference electrode 18 includes the IR drop or voltage drop attributable to the corrosion currents which are generated due to the corrosion of reinforcement 20. Valving is used to change the voltage measurement paths. Initially a voltage reading (baseline reading) is taken by measuring the freely corroding potential of wire electrode 11 relative to the reference electrode 18. Base 16 is then sealed to surface 14 of concrete structure 15 making the opening 22 through the base of probe 10 the lowest resistance path between the two electrodes. A second voltage reading is taken with the change in the voltage V being the IR drop attributable to the electrochemical currents generated as a result of the corrosion of reinforcement 20, as illustrated in FIG. 2.

Figure 3:
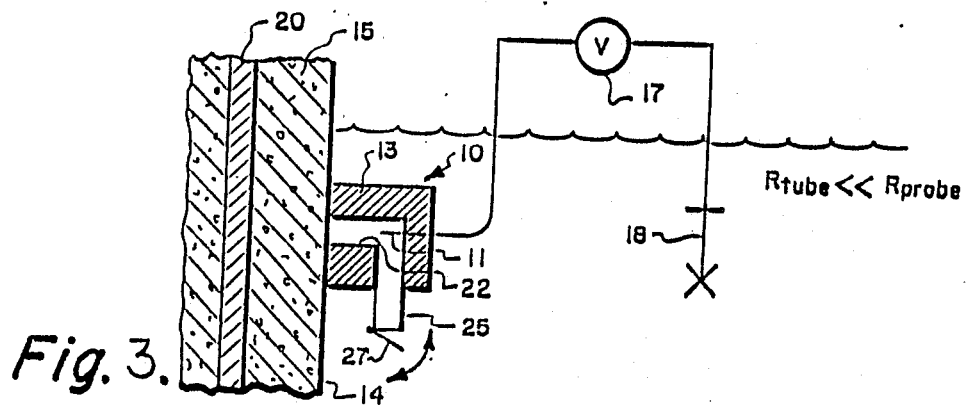
FIG. 3 is a schematic diagram showing one valving arrangement for determining IR drop magnitude in the system of FIG. 2.

One possible mechanical valving arrangement for determining the magnitude of the IR drop is illustrated in FIG. 3.

As shown in FIG. 3, a tubular section 25 communicating to the interior of probe 10, with a means, such as flap 27, operates to provide a path through the probe housing to the seawater outside. Any suitable means, not shown, can be used to open and close flap 27. With flap 27 open, the resistance path from electrode 11 via the water path through tube 25 to reference electrode 18 is much less than the resistance path from electrode 11 via the probe housing and concrete structure 15 to reference electrode 18 with the flap closed.

Pit Location

The magnitude of V will be proportional to the detected current flow, given a constant path resistance ($R_p$). Assuming this to be true, active corrosion sites (anodic sites) may be located by simple surface surveys. V will be greater directly over corrosion pits. Here current density will be greatest and assuming current radiating from the pit, all current (positive) will flow from the center outward relative to the probe base, such as illustrated in FIG. 4. With distance from the pit, current density is diminished and there is flow in two directions relative to the probe circumference. Therefore, V is high over the pit due to higher current density and additive current elements.

In practice $R_p$ can vary greatly and it is necessary to determine corrosion current values to locate active areas.

Corrosion Current

In order to derive the current flow associated with V, the resistance of the volume of concrete observed by the probe must be determined. This is accomplished by an auxiliary electrode 51 placed in the surface probe 10 along with electrode 11, as shown in FIG. 5. Electrode 51 is connected through a power source 53 to an external counter electrode 55.

The shift in the primary electrode 11 potential for a given current is then determined. This can be done for a range of currents to produce a calibration curve, or to verify linearity and calculate probe/interface resistance. For proper operation the induced current should "see" the same volume of concrete as the current between the primary electrode 11 and the reference electrode 18. Then the current associated with the IR drop can be calculated.

$$I_{det} = \frac{V}{R_p}$$

$I_{det}$ has proven to be proportional to total pitting current; however, the exact detection boundaries are uncertain.

Output Instrumentation

Probe response is readily determined from a strip chart recording. Initial voltage is nulled with a counter-voltage to where small (i.e. less than 0.1 mV) changes with valving can be detected. A buffer amplifier 58 is used between the probe 11 and recorder 59 to prevent polarization of the electrodes.

With a movable probe 10 used in surveys, $R_p$ varies with surface 14 irregularities and the interface pressure between probe 10 and the concrete structure 15. In survey applications, $R_p$ can be monitored continuously through input of a fixed current pulse $I_p$ from power source 53 through the auxiliary electrode 51. Since measured response to this current input and the response to any detectable IR drop are both functions of $R_p$, $I_{det}$ at a particular location is simply the pulse current times the ratio of V to the voltage shift produced by the pulse. Typical recorder output is shown in FIG. 6, by way of example. FIG. 6 shows the pulse voltage shift (small fluctuations) superimposed on V for fourteen locations (the large shifts mumbered 1 to 14).

The concrete reinforcement inspection probe system provides a simple means for investigating corrosion activity in concrete structures. No electrical contact with the reinforcement rebar, etc. is required, eliminating any need for concrete removal to make a connection. Surveys using the present device can locate anodic areas underwater where conventional potential measurements give only an overall potential. In the present system current is measured directly, giving an account of instantaneous activity as opposed to merely corrosion history.

Numerous probe 10 sizes, base 16 configurations, and construction materials can be used to suit particular applications. Small probes are more accurate for locating active pits; however, more sites need to be tested to center the probe electrode over a pit for maximum V. A loss in resolution and sensitivity may be required in obtaining a probe size practical for large scale surveys.

What is claimed is:

1. A method for nondestructive detecting, locating and measuring of the corrosion activity of a metal reinforcement in a concrete marine structure by direct detection of electrochemical current flow, comprising the steps of:
   a. first, establishing a baseline potential by measuring the freely corroding electrical potential of a probe electrode relative to a remote underwater reference electrode;
   b. secondly, positioning said probe electrode in sealing engagement against the underwater surface of said concrete structure such that the measurement path is effectively restricted to the path from said probe electrode through said concrete structure and surrounding water to said remote electrode, and then measuring the electrical potential between said probe electrode and said remote reference electrode; the potential difference between the first and second potential measurements being the IR drop caused by corrosion currents flowing through said concrete structure, and attributable to the electrochemical corrosion of said metal reinforcement.

* * * * *